United States Patent
Bonnard et al.

(10) Patent No.: US 6,696,590 B2
(45) Date of Patent: Feb. 24, 2004

(54) PROCESS FOR THE SYNTHESIS OF ALIPHATIC, CYCLOALIPHATIC OR ARALIPHATIC CHLOROFORMATES

(75) Inventors: Hubert Bonnard, La Ferte Alais (FR); Laurence Ferruccio, Vert le Grand (FR); Patricia Gauthier, La Ferte Alais (FR); Jean-Pierre Senet, Chapelle la Reine (FR)

(73) Assignee: SNPE, Paris Cedex (FR)

( * ) Notice: Subject to any disclaimer, the term of this patent is extended or adjusted under 35 U.S.C. 154(b) by 0 days.

(21) Appl. No.: 10/022,963

(22) Filed: Dec. 18, 2001

(65) Prior Publication Data

US 2002/0082444 A1 Jun. 27, 2002

(30) Foreign Application Priority Data

Dec. 22, 2000 (FR) .............................. 00 16880

(51) Int. Cl.$^7$ .............................. C07C 69/96

(52) U.S. Cl. ...................... 558/280; 558/282

(58) Field of Search ................ 558/280, 282

(56) References Cited

U.S. PATENT DOCUMENTS

| 3,419,543 A | 12/1968 | Mold et al. ................. 260/234 |
| 5,703,123 A | 12/1997 | Pelzer et al. ................ 514/512 |
| 6,036,925 A | 3/2000 | Adams et al. ............... 422/126 |

FOREIGN PATENT DOCUMENTS

| EP | 0075145 | | 8/1982 |
| FR | 1431961 | * | 2/1966 |
| FR | 2484406 | | 6/1981 |

OTHER PUBLICATIONS

Cycloaddition Routes to Tricyclo . . . , Lee Et al., J. Org.Chem., vol. 58, pp. 2186–2195 (1993).
Synthesis of Conduramines from N–tert–Butoxycarbonylpyrrole, Leung–Toung Et al., J. Org.Chem., vol. 63, pp. 3225–3250 (1998).
New Acylnitroso Compounds For the Asymmetric Oxyamination of Dienes, Gouverneur, Tetrohedron, vol. 54, pp. 10537–10554 (1998).
Lewis Acid–Promoted Asymmetric Conjugate Allylation . . . Sato, Et al, Tetrahedron Letters, vol. 37, pp. 9063–9066 (1966).
Facile Chloride Substitution of Activated Alcohols by Triphosgene, Goren, Et al, J. Org. Chem., vol. 56, pp. 7186–7188 (1991).
Total Synthesis of (–)–Epibatidine Using an Asymmetric Diels–Alder Reaction . . . , Aoyagi Et al, J. Org. Chem., vol. 63, pp 8397–8406 (1998).
Hydrogen Transfer from Alcohols to Carbonyl Compounds . . . Konishi, Et al, J. Org. Chem., vol. 55, pp. 816–820 (1990).
NMR Detection of N–Acyliminium Ion Intermediates . . . , Yamamoto Et al, J. Org. Chem., vol. 114, pp. 121–125 (1992).

* cited by examiner

*Primary Examiner*—Johann Richter
*Assistant Examiner*—Paul A. Zucker
(74) *Attorney, Agent, or Firm*—Buckname & Archer

(57) ABSTRACT

The disclosure relates to a process for the synthesis of substituted or unsubstituted aliphatic, cycloaliphatic or araliphatic chloroformates by reaction of the corresponding alcohol with phosgene, diphosgene and/or triphosgene. The reaction is carried out under a pressure of between $15 \times 10^3$ Pa and $85 \times 10^3$ Pa and at a temperature of between $-30°$ C. and $+50°$ C. The process is particularly well suited to the preparation of menthyl chloroformate and benzyl chloroformate.

8 Claims, No Drawings

PROCESS FOR THE SYNTHESIS OF ALIPHATIC, CYCLOALIPHATIC OR ARALIPHATIC CHLOROFORMATES

The present invention relates to a process for the synthesis of substituted or unsubstituted aliphatic, cycloaliphatic or araliphatic chloroformates.

It relates more particularly to a process for the improved synthesis of these chloroformates by phosgenation of the corresponding alcohols.

Chloroformates are synthetic intermediates which are very useful in the pharmaceutical, cosmetic and food industries.

Mention will in particular be made of benzyl chloroformate, one of the starting materials in the synthesis of Z-aspartic acid, which compound is used in the manufacture of aspartame.

Another very important chloroformate is menthyl chloroformate, a compound used for its menthol taste. It is encountered as synthetic intermediate in the tobacco industry and in the pharmaceutical industry.

Processes for the synthesis of chloroformates from phosgene and the corresponding alcohol are already known to a person skilled in the art. The problem encountered during such syntheses is the production of hydrochloric acid, which leads to the formation of by-products.

A first solution to this problem is to add a base, such as a tertiary amine, to the reaction medium. A synthesis of menthyl chloroformate is thus described in a paper in the Journal of Organic Chemistry of 1993 (Vol. 58, No. 8, 2186–2195): The reaction of menthol and of phosgene is carried out in toluene, in the presence of quinoline.

Another paper in the Journal of Organic Chemistry of 1998 (Vol. 63, 3235–3250) describes a synthesis of menthyl chloroformate from phosgene and menthol also involving a base, pyridine. The disadvantages related to such syntheses are not only the additional cost, due to the use of a base, but also the need to remove the amine hydrochloride formed, in particular by direct filtration or by washing the organic phase with water. This results in a longer and more expensive process.

Other synthetic routes not involving a base have also been provided. Thus, U.S. Pat. No. 3,419,543 discloses a base-free process for the synthesis of menthyl chloroformate from phosgene and a solution of menthol in cyclopentane. In the reaction thus described, the constituents are introduced at −75° C. This very low temperature is a disadvantage as it is difficult to obtain industrially, requiring specific and very expensive equipment.

Another synthetic route was then proposed, at a higher temperature and not involving a base either. A paper which appeared in Volume 54 of Tetrahedron in 1998 (Tetrahedron, 54 (1998), 10537–10534) discloses such a synthesis: phosgene reacts at −10° C. with menthol in toluene. Menthyl chloroformate is obtained with a yield of only 82%.

Furthermore, these processes, at atmospheric pressure and without a base, exhibit very slow reaction kinetics, which is a disadvantage industrially.

A person skilled in the art is therefore constantly on the lookout for an inexpensive process for the synthesis of aliphatic, cycloaliphatic or araliphatic chloroformates which has rapid kinetics and a high yield and which gives products of very high purity.

Such a process is a subject-matter of the present invention.

The invention relates to a process for the synthesis of substituted or unsubstituted aliphatic, cycloaliphatic or araliphatic chloroformates by reaction of the corresponding alcohol with phosgene, diphosgene and/or triphosgene, characterized in that the reaction is carried out under a pressure of less than or equal to $95\times10^3$ Pa, i.e. under a pressure of less than or equal to 950 mbar.

This process exhibits the advantage of being simple and inexpensive. The chloroformates are rapidly obtained with a very high yield, generally of greater than 97%, and have good purity, generally of the order of 97%, indeed even 99%. Very little in the way of by-products is obtained. This result is all the more surprising since vacuum is commonly used to remove phosgene from the reaction medium. Degassing during the reaction should therefore result in a shortfall in phosgene. It is known that, in this case, the alcohol reacts with the chloroformate already formed to give a carbonate. Furthermore, as the reaction rate is a function of the concentration of phosgene, the kinetics should have become slower.

This process makes it possible to obtain substituted or unsubstituted aliphatic, cycloaliphatic or araliphatic chloroformates which can be prepared by phosgenation of the corresponding alcohols. In particular, it makes it possible to obtain $C_1$ to $C_{20}$ aliphatic, $C_4$ to $C_{20}$ cycloaliphatic or $C_7$ to $C_{20}$ araliphatic chloroformates which are saturated or unsaturated and substituted or unsubstituted, the substituents being groups which are unreactive with respect to phosgene and to hydrochloric acid. This process is particularly well suited to the preparation of secondary or tertiary aliphatic or cycloaliphatic chloroformates and of araliphatic chloroformates. In a particularly preferred way, this process makes it possible to obtain menthyl chloroformate and benzyl chloroformate.

The reaction is carried out at a temperature of between −30° C. and +50° C. and preferably between −10° C. and +20° C.

According to a preferred alternative form of the invention, the reaction is carried out under a pressure of between $5\times10^3$ Pa and $95\times10^3$ Pa, i.e. between 50 mbar and 950 mbar, and better still under a pressure of between $15\times10^3$ Pa and $85\times10^3$ Pa, i.e. between 150 mbar and 850 mbar.

In a particularly preferred way, the reaction is carried out under a pressure of between $35\times10^3$ Pa and $75\times10^3$ Pa, i.e. between 350 mbar and 750 mbar.

Phosgene, diphosgene and/or triphosgene can be used. Preferably, phosgene is used. The amount of phosgene, diphosgene and/or triphosgene introduced is generally such that there is between 1 and 10 molar equivalents of phosgene with respect to the alcohol and preferably between 1.5 and 2.5 molar equivalents.

As diphosgene and triphosgene respectively generate 2 and 3 mol of phosgene, the amount used will be between, respectively, 0.5 and 5 mol, preferably between 0.75 and 1.25 mol, for diphosgene and between 0.3 and 3.3 mol, preferably between 0.5 and 0.8 mol, for triphosgene.

The reaction can be carried out with or without solvent. One of the compounds of the reaction, the chloroformate or the phosgene, can be used as solvent. The reaction is preferably carried out in the presence of an inert solvent chosen from the group consisting of chlorinated or nonchlorinated aliphatic hydrocarbons, chlorinated or nonchlorinated aromatic hydrocarbons, esters and ethers.

Mention may be made, as aliphatic hydrocarbons, of methylene chloride, chloroform, heptane or pentane.

Mention may be made, as aromatic hydrocarbons, of toluene or xylene. Use may also be made of esters, such as, for example, ethyl acetate or isopropyl acetate but also of methyl carbonate.

Ethers can also be used as inert solvent; they are, inter alia, ethyl and diisopropyl ethers.

This process is particularly well suited to the preparation of menthyl chloroformate and benzyl chloroformate, obtained respectively by reaction of menthol and benzyl alcohol with phosgene.

The phosgene is introduced into the reactor preferably at a temperature of less than 8° C. and under a pressure of between $35 \times 10^3$ Pa and $75 \times 10^3$ Pa, i.e. between 350 mbar and 750 mbar.

When all the phosgene has been introduced, the reactants are left in contact, preferably for a period of time of between 2 and 8 hours, at a temperature preferably of between −10° C. and 20° C.

Menthyl chloroformate of very high purity, of the order of 99%, and with a yield of greater than 97% is obtained. Less than 0.5% by weight of menthol and only traces of menthyl chloride and of bismenthyl carbonate are found in it.

Benzyl chloroformate is also obtained with good purity of greater than 97%. Thus, benzyl chloride is only present therein in a proportion of 0.5% by weight or less and dibenzyl carbonate is only present therein in an amount of less than 0.3% by weight.

The low level of these impurities, and in particular of benzyl chloride, is highly advantageous. This is because benzyl chloride is a highly reactive compound and is consequently a nuisance in some applications of benzyl chloroformate and in particular in syntheses of amino acids.

The following examples illustrate, without implied limitation, alternative embodiments of the invention.

EXAMPLE 1

Synthesis of Menthyl Chloroformate Under 500 mbar and at a Temperature of Between −3° C. and 20° C.

The reaction is carried out in a 500 ml jacketed reactor. This reactor is equipped with a reflux condenser surmounted by a dry ice trap. Two columns, filled with charcoal and connected to the assembled apparatus thus formed, are used to trap the phosgene and the hydrochloric acid given off during the reaction.

14.9 g of toluene and 50.4 g of (L)-menthol, i.e. 0.322 mol of menthol, are introduced into the reactor. The medium is cooled to approximately −3° C.–0° C. 65 g of phosgene, i.e. 0.650 mol, are then gradually introduced under a pressure of 500 mbar. The amount of phosgene is thus 2 molar equivalents with respect to the menthol.

After introducing all the phosgene, the reaction medium is gradually reheated. This operation is carried out under a pressure of 500 mbar. The temperature changes from −3° C. to +7° C. over 4 hours and then from 7° to 19° C. over 50 minutes and, finally, the temperature is maintained at 19° C. for 20 minutes. The product obtained is subsequently degassed at this temperature.

70 g of (L)-menthyl chloroformate, i.e. 0.320 mol, are obtained, which corresponds to a yield of 99%.

The product obtained is analysed by gas chromatography. The purity of the chloroformate is 99%, and less than 0.5% by weight of menthol and 250 ppm of menthyl chloride are found. Bismenthyl carbonate is not detected.

EXAMPLE 2

Synthesis of Menthyl Chloroformate Under 500 mbar and at a Temperature of Between 8° C. and 19° C.

The assembled apparatus used is the same as that in Example 1.

93.4 g of toluene and 315.8 g of menthol, i.e. 2 mol, are introduced into the reactor. 308 g of phosgene, i.e. 3.1 mol, i.e. 1.55 molar equivalents with respect to the menthol, are gradually added under a pressure of 500 mbar and at a temperature of between 8° C. and 15° C.

At the end of the introduction, the reaction is continued for a further 6.5 hours at a temperature of between 12° C. and 19° C. and under a pressure of 500 mbar.

435 g of menthyl chloroformate, i.e. 1.99 mol, are obtained, which corresponds to a yield of 99%.

The product obtained is analysed by gas chromatography. The purity of the chloroformate is 99.7%, and less than 0.3% of menthol and less than 150 ppm of menthyl chloride are found. Bismenthyl carbonate is not detected.

EXAMPLE 3

Synthesis of Benzyl Chloroformate Under 500 mbar.

The assembled apparatus used is the same as that in Example 1.

217 g of alcohol, i.e. 1.99 mol, are introduced into the reactor. The medium is cooled to approximately 0° C.

250 g of phosgene, i.e. 2.52 mol, are then gradually introduced under a pressure of 500 mbar and at a temperature of between 0° C. and 6° C. The amount of phosgene used is 1.27 molar equivalents with respect to the alcohol.

The total duration of the reaction is 6.5 hours.

275 g of benzyl chloroformate, i.e. 1.61 mol, are obtained, which corresponds to a yield of 81%.

The product obtained is analysed by gas chromatography. The purity of the chloroformate is 98.4%. The final product comprises 0.4% of benzyl alcohol, 0.51% of benzyl chloride and 0.26% of dibenzyl carbonate.

EXAMPLE 4

Synthesis of Benzyl Chloroformate Under 250 mbar.

The synthesis is carried out in the same way as in Example 3. It is carried out under a pressure of 250 mbar.

The amounts of reactants used are as follows:

223 g of benzyl alcohol, i.e. 2.06 mol, and 275 g of phosgene, i.e. 2.77 mol.

At the end of the introduction of phosgene, the reaction is continued for a further 2 hours.

263 g of benzyl chloroformate, i.e. 1.54 mol, are obtained, which corresponds to a yield of 75%.

The product obtained is analysed by gas chromatography. The purity of the chloroformate is 97.1%.

The final product comprises 0.02% of benzyl alcohol, 0.27% of benzyl chloride and 0.29% of dibenzyl carbonate.

TEST AT ATMOSPHERIC PRESSURE

Synthesis of Methyl Chloroformate.

This test does not form part of the invention; it was carried out for the purpose of showing that the fact of operating under reduced pressure does not correspond to an arbitrary choice but corresponds to a selection necessary in order to obtain the desired technical effect.

108 g of toluene and 100 g of menthol, i.e. 0.63 mol of menthol, are introduced into the reactor. 89 g of phosgene, i.e. 0.9 mol, i.e. 1.4 molar equivalents with respect to the menthol, are introduced into the reactor.

The phosgene is introduced at atmospheric pressure and at a temperature of between −8° C. and +8° C. The reaction is continued for a further period of just over 4 hours at a temperature of between −5° C. and +5° C.

93.4 g of menthyl chloroformate, i.e. 0.427 mol, are obtained, which corresponds to a yield of 68%. The main impurity present in this product is unreacted starting menthol; it is present in a proportion of 33% by weight.

What is claimed is:

1. A process for the synthesis of menthyl chloroformate or benzyl chloroformate by reaction of the corresponding alcohol with phosgene, diphosgene and/or triphosgene, wherein the reaction is carried out under a pressure of between $15 \times 10^3$ Pa and $85 \times 10^3$ Pa; and at a temperature of between −10° C. and +20° C.

2. The process according to claim 1, wherein the reaction is carried out under a pressure of between $35 \times 10^3$ Pa and $74 \times 10^3$ Pa.

3. The process according to claim 1, wherein the reaction is carried out in the presence of an inert solvent chosen from the group consisting of chlorinated or non-chlorinated aliphatic hydrocarbons, chlorinated or non-chlorinated aromatic hydrocarbons, esters and ethers.

4. The process according to claim 1, wherein phosgene is used.

5. The process according to claim 1, wherein the amount of phosgene, diphosgene and/or triphosgene used is such that there is between 1 and 10 molar equivalents of phosgene with respect to the alcohol.

6. The process according to claim 5, wherein the amount of phosgene, diphosgene and/or triphosgene used is such that there are between 1.5 and 2.5 molar equivalents of phosgene with respect to the alcohol.

7. The process according to claim 1, wherein the chloroformate obtained is menthyl chloroformate.

8. The process according to claim 1, wherein the chloroformate obtained is benzyl chloroformate.

* * * * *